(12) United States Patent
Kawaletz

(10) Patent No.: US 9,410,921 B2
(45) Date of Patent: Aug. 9, 2016

(54) METHOD FOR TESTING A CMOS TRANSISTOR

(71) Applicant: Micronas GmbH, Freiburg (DE)

(72) Inventor: Oliver Kawaletz, Eichstetten (DE)

(73) Assignee: Micronas GmbH, Freiburg (DE)

( * ) Notice: Subject to any disclaimer, the term of this patent is extended or adjusted under 35 U.S.C. 154(b) by 5 days.

(21) Appl. No.: 14/664,221

(22) Filed: Mar. 20, 2015

(65) Prior Publication Data

US 2015/0268190 A1 Sep. 24, 2015

(30) Foreign Application Priority Data

Mar. 20, 2014 (DE) .......................... 10 2014 003 962

(51) Int. Cl.
| | |
|---|---|
| *G01R 31/26* | (2014.01) |
| *G01N 27/414* | (2006.01) |
| *G01R 31/265* | (2006.01) |
| *G01R 31/312* | (2006.01) |

(52) U.S. Cl.
CPC ........ *G01N 27/4143* (2013.01); *G01N 27/4148* (2013.01); *G01R 31/265* (2013.01); *G01R 31/2621* (2013.01); *G01R 31/312* (2013.01)

(58) Field of Classification Search
CPC ......... H01L 22/00; H01L 22/10; H01L 22/14; H01L 22/20; H01L 22/30; H01L 22/32; H01L 22/34; G01N 27/4148; G01N 27/4141; G01N 27/4143; G01R 31/2601; G01R 31/2621; G01R 31/26; G01R 31/265
See application file for complete search history.

(56) References Cited

U.S. PATENT DOCUMENTS

| | | | | |
|---|---|---|---|---|
| 5,301,159 A | * | 4/1994 | Lee .......................... | G11C 17/18 257/50 |
| 8,592,875 B2 | * | 11/2013 | Wilbertz ................. | H01L 29/66 257/253 |
| 2002/0005723 A1 | * | 1/2002 | Oishi .................. | G01R 31/2879 324/530 |
| 2003/0006413 A1 | | 1/2003 | Chawla et al. | |
| 2008/0029762 A1 | * | 2/2008 | Schroeder ............... | H01L 22/14 257/48 |

FOREIGN PATENT DOCUMENTS

| | | |
|---|---|---|
| DE | 10 2005 029 105 A1 | 1/2007 |
| DE | 10 2011 118 930 A1 | 5/2013 |

OTHER PUBLICATIONS

William Mann, "Leading Edge of Wafer Level Testing" [Online, Powerpoint Presentation], 2004 ITC Program Committee, [Retrieved Dec. 10, 2015], Retrieved from http://www.swtest.org/swtw_library/2004proc/PDF/T00_01_Mann.pdf.*

* cited by examiner

*Primary Examiner* — Zandra Smith
*Assistant Examiner* — Evan Clinton
(74) *Attorney, Agent, or Firm* — Muncy, Geissler, Olds & Lowe, P.C.

(57) ABSTRACT

A method for testing a CMOS transistor with an electrical testing unit, the CMOS transistor being formed in a semiconductor substrate of a semiconductor wafer. A plurality of CMOS transistors are formed on the semiconductor wafer and the electrical testing unit has a support plate and a metal layer formed on the support plate. The CMOS transistor having a first terminal contact, a second terminal contact and a third terminal contact, the second terminal contact configured as an electrically open control contact and in a process step the metal layer is positioned above the semiconductor wafer over the control contact and a potential difference between the first terminal contact and a third terminal contact is generated. The control contact is capacitively coupled by applying a drive potential to the metal layer, and the function of the CMOS transistor is tested by measuring an electrical variable dependent on the capacitive coupling.

17 Claims, 2 Drawing Sheets

METHOD FOR TESTING A CMOS TRANSISTOR

This nonprovisional application claims priority under 35 U.S.C. §119(a) to German Patent Application No. 10 2014 003 962.5, which was filed in Germany on Mar. 20, 2014, and which is herein incorporated by reference.

BACKGROUND OF THE INVENTION

1. Field of the Invention

The present invention relates to a method for testing a CMOS transistor.

2. Description of the Background Art

A test system for testing semiconductor wafers is known from U.S. 2003 000 6413 A1. Further, a contacting device for connecting a test sample to an electrical testing unit is known from DE 10 2005 029 105 A1.

SUMMARY OF THE INVENTION

It is therefore an object of the present invention to provide a device that refines the prior art.

According to an embodiment of the invention, a method for testing a CMOS transistor is provided, comprising an electrical testing unit, whereby the CMOS transistor is formed in a semiconductor substrate of a semiconductor wafer, and whereby a plurality of CMOS transistors are formed on the semiconductor wafer, and whereby the electrical testing unit has a support plate and a metal layer or an electrically conductive layer is formed on the support plate, and whereby the CMOS transistor has a first terminal contact and a second terminal contact and a third terminal contact, whereby the second terminal contact is configured as an electrically open control contact and in a process step the metal layer is positioned above the semiconductor wafer over the control contact and in a further process step a potential difference between the first terminal contact and a third terminal contact is generated and in a further process step the control contact is capacitively coupled by applying a drive potential to the metal layer, and in a process step the function of the CMOS transistor is tested by measuring an electrical variable dependent on the capacitive coupling. It can be understood that the open control terminal can also be known under the term "floating gate." In this regard, the open control terminal comprises a region made by a planar trace, whereby the width of the region is at least 20 µm. The planar trace region comprises a value between 0.2 mm$^2$ and 1 mm$^2$. It is understood, further, that the first terminal contact and the second terminal contact of the CMOS transistor can be understood to be either the source terminal or the drain terminal of the CMOS transistor. It should also be noted that the testing of the CMOS transistor can be carried out at the so-called "wafer level"; i.e., the semiconductor wafer is not yet sawn. During the testing of CMOS transistors, the semiconductor wafer lies on a support called a "chuck." It should be noted, further, that an integrated circuit is also preferably formed on the semiconductor wafer and integrated monolithically with the CMOS transistors. It is preferred in particular that there is an electrical functional connection between the integrated circuit and the CMOS transistor. It should be noted, further, that in the present case the conductive layer also comprises a metal layer.

An advantage of the method of the invention is that the individual CMOS transistors, which have an open control terminal, are tested electrically immediately after the processing of the semiconductor wafer. As a result, failures can be detected even before the dicing of the CMOS transistors. A cost-intensive assembly of the failed CMOS transistors can be avoided. A further advantage is that the open control contact is driven without contact by means of the capacitive effect from a metal layer or an electrically conductive layer. Because of this, a voltage can be applied to the gate of the CMOS transistor, so that the CMOS transistor is through-connected.

In an embodiment, the value of the drive potential can be varied to obtain a characteristic of the electrical variable. A reliable conclusion on the electrical function of the CMOS transistor can be obtained with the recording of the characteristic. Tests have shown that the drive potential can be varied within a range from minus twenty volts to plus twenty volts. Both the p-channel and the n-channel of CMOS transistors can be tested in this way. Furthermore, the value of leakage currents and the value of the channel resistance of the CMOS transistor can be determined from the characteristic. In order to keep the data volume of the measured values low, it is preferred to vary the drive potential in 5-volt steps. As a result, the function of the CMOS transistors can be reliably tested with a few measured values and a short measuring time. It is understood that other drive potential steps or a continuous traversing of the voltage range is also advantageous.

In an embodiment, the third terminal contact is connected to a ground potential. In a further refinement, the current flow between the first terminal contact and the third terminal contact and/or the voltage at an output terminal connected to the first terminal contact are measured as the electrical variable.

In an embodiment, the support plate has a ceramic connection. As a result, the surface cannot be statically charged in an insulated manner. Preferably, the electrical testing unit comprises a probe card, whereby the first terminal contact is contacted by means of the probe card and supplied with a voltage. It is advantageous, if for contacting the CMOS transistor the probes of the probe card are passed through openings in the support plate. Tests have shown that even two probes are sufficient to measure a CMOS with an open gate, whereby in each case one of the two probes is connected to the source and the other probe to the drain of the transistor. It is preferred, further, if the metal layer contains the elements titanium and/or silver and is made in the shape of a trace. It is understood that one electrically conductive layer is also sufficient and is preferably made in the shape of a trace. With the trace-shaped design the control contacts can be driven simultaneously also in the case of a plurality of CMOS transistors, without the entire surface of the support plate being covered with a metal layer. Tests have shown that the support plate is preferably smaller than 6 cm$^2$ in size and in particular the metal surface on the support plate comprises less than 70% of the surface of the support plate.

In an embodiment, the CMOS transistor can be made as a gas-sensitive SGFET or gas-sensitive CCFET, whereby the second terminal contact comprises a plate-shaped metal layer and the metal surface of the support plate is positioned above the metal layer.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein:

FIG. 1b shows an enlarged detail of a cross-sectional illustration of the illustration in FIG. 1a;

DETAILED DESCRIPTION

Figure 1A:
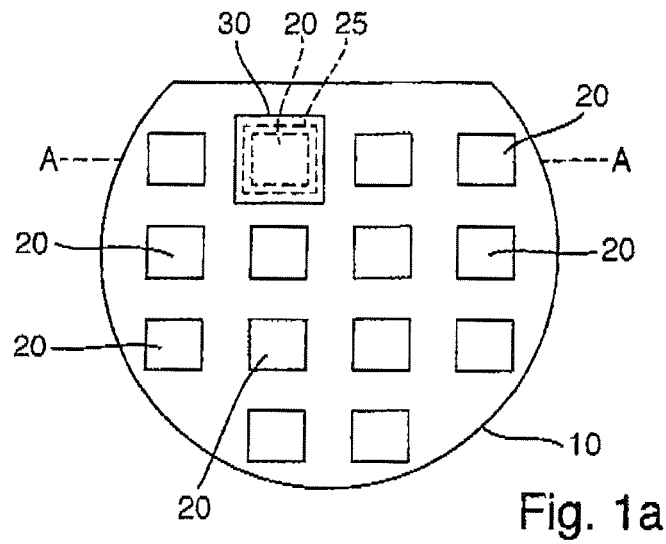
FIG. 1a shows a top plan view of a semiconductor wafer.

The illustration in FIG. 1a shows a semiconductor wafer 10 with a plurality of CMOS transistors 20. CMOS transistors 20 each have an open control input, also called a "floating gate" (not shown). A support plate 25 is arranged as part of a testing unit 30 above one of CMOS transistors 20. Support plate 25 is made of ceramic. In the present case, the CMOS transistors are made as SGFET or CCFET and represent part of an integrated circuit that is not shown. For reasons of clarity, testing unit 30 is not shown in detail. After the particular CMOS transistor 20 has been tested, the testing unit is positioned above the next CMOS transistor 20.

Figure 1B:
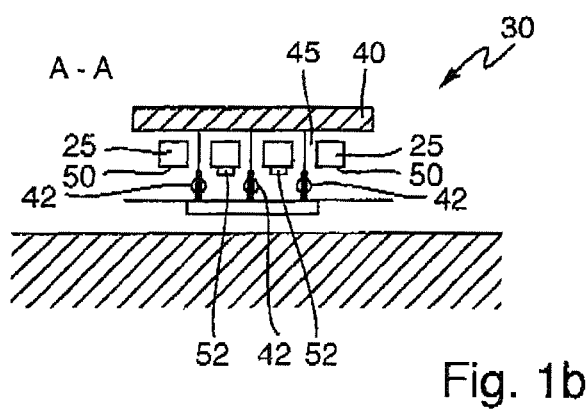

The illustration in FIG. 1b shows an enlarged detail in a cross-sectional illustration of the illustration in FIG. 1a. Only the differences relative to the illustration in FIG. 1a will be described below. A probe holder 40 with three probes 42 is formed above support plate 25. The three probes 42 each reach through an opening 45 in support plate 25 and contact metallic surfaces (not shown), which are also called "pads," on the surface of semiconductor wafer 10, in order to contact CMOS transistor 20 via the metallic surfaces. A metal layer 52 or at least one electrically conductive layer is formed on bottom side 50 of support plate 25, whereby metal layer 52 is connected electrically to a reference potential. Support plate 25 or an electrically conductive layer with metal layer 52 is positioned directly above the open control contact, in order to achieve a good capacitive coupling between metal layer 52 and the open control contact.

Figure 2:
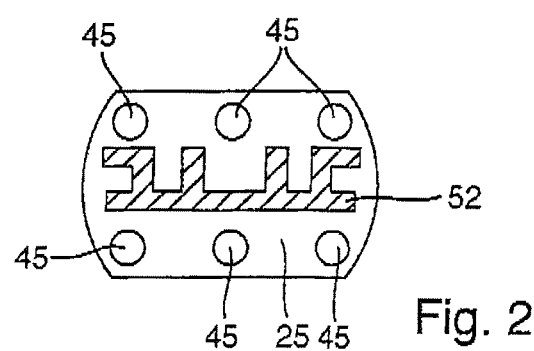
FIG. 2 shows a top plan view of a support plate.

The bottom side of support plate 25 is shown in a top plan view in FIG. 2. Only the differences to the explanations in relation to the illustration in the previous figures will be indicated below. Support plate 25 has a total of six openings 45 through which probes 42 extend. Metal layer 52 is formed in the shape of a trace and covers a greater part of the bottom side of support plate 25.

Figure 3:
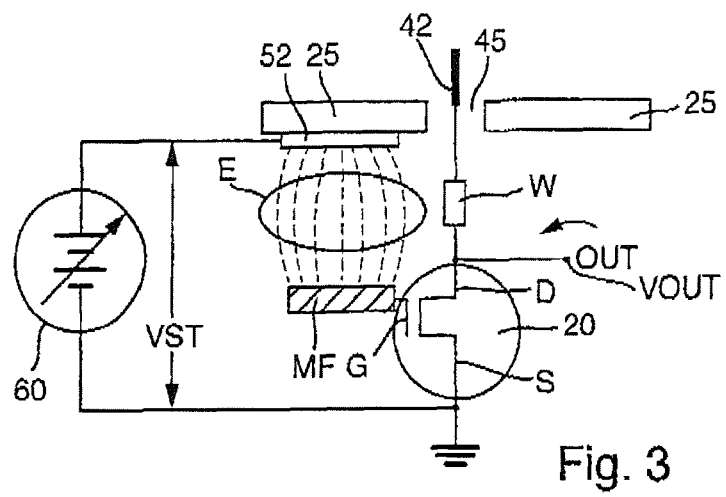
FIG. 3 shows an equivalent circuit of the measuring setup for carrying out the method.

An equivalent circuit of the measuring setup for carrying out the method is shown in FIG. 3. Only the differences to the explanations in relation to the illustration in the previous figures will be indicated below. An adjustable direct voltage of voltage source 60 is applied between metal layer 52 and the third terminal contact which in the present case is made as a source contact S of CMOS transistor 20. The second control terminal is made as gate G of CMOS transistor 20 and has a plate-shaped metal surface MF. The first metal contact, which in the present case is made as drain contact D, is connected to an output contact OUT and via a resistor W to the testing unit, which is not shown. If as shown a voltage is applied to metal layer 52, an electric field E forms between the plate-shaped metal surface MF and metal layer 52. The resulting voltage is also applied directly to the third terminal contact. If the voltage is sufficient, a channel region forms in the CMOS transistor and the CMOS transistor becomes conductive.

Figure 4:
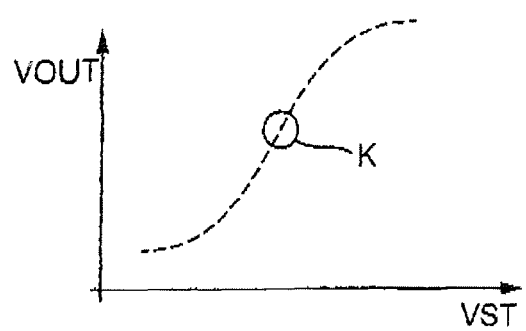
FIG. 4 shows a characteristic curve for an electrical variable, to be tested, of the CMOS transistor.

A characteristic curve of a variable to be tested is shown in FIG. 4. Only the differences to the explanations in relation to the illustration in the previous figures will be indicated below. The course of the output voltage VOUT at the output contact OUT versus the voltage VST applied to metal layer 52 is shown in the present case. It is evident that the output voltage VOUT increases nearly proportionally with an increasing value of the applied voltage VST in a middle region of the characteristic curve K.

The invention being thus described, it will be obvious that the same may be varied in many ways. Such variations are not to be regarded as a departure from the spirit and scope of the invention, and all such modifications as would be obvious to one skilled in the art are to be included within the scope of the following claims.

What is claimed is:

1. A method for testing a CMOS transistor with an electrical testing unit, the method comprising:

forming the CMOS transistor in a semiconductor substrate of a semiconductor wafer, the CMOS transistor having a first terminal contact and a second terminal contact and a third terminal contact, the second terminal contact being configured as an electrically open control contact, wherein at least two CMOS transistors are formed on the semiconductor wafer;

providing the electrical testing unit with a support plate;

forming a conductive layer on the support plate;

positioning the conductive layer above the semiconductor wafer over the control contact;

generating a potential difference between the first terminal contact and a third terminal contact;

capacitively coupling the control contact to the electrical testing unit by applying a drive potential to the conductive layer to test the CMOS transistor; and testing a function of the CMOS transistor by measuring an electrical variable dependent on the capacitive coupling.

2. The method for testing a CMOS transistor according to claim 1, wherein a value of the drive potential is varied to obtain a characteristic of the electrical variable.

3. The method for testing a CMOS transistor according to claim 1, wherein the drive potential is varied within a range from minus twenty volts to plus twenty volts.

4. The method for testing a CMOS transistor according to claim 3, wherein the drive potential is varied in 5-volt steps.

5. The method for testing a CMOS transistor according to claim 1, wherein the third terminal contact is connected to a ground potential.

6. The method for testing a CMOS transistor according to claim 1, wherein a current flow between the first terminal contact and the third terminal contact or a voltage at an output terminal connected to the first terminal contact is measured as the electrical variable.

7. The method for testing a CMOS transistor according to claim 1, wherein the support plate has a ceramic connection.

8. The method for testing a CMOS transistor according to claim 1, wherein the electrical testing unit comprises a probe card, and wherein the first terminal contact is contacted via the probe card and supplied with a voltage.

9. The method for testing a CMOS transistor according to claim 1, wherein, for contacting the CMOS transistor, the probes of the probe card are passed through openings in the support plate.

10. The method for testing a CMOS transistor according to claim 1, wherein the conductive layer comprises titanium and/or silver and is made in the shape of a trace.

11. The method for testing a CMOS transistor according to claim 1, wherein the support plate is smaller than 6 $cm^2$ in size, and wherein the conductive layer on the support plate comprises less than 70% of the area of the support plate.

12. The method for testing a CMOS transistor according to claim 1, wherein the CMOS transistor is made as a gas-sensitive SGFET or gas-sensitive CCFET, wherein the second terminal contact comprises a plate-shaped metal surface, and wherein the conductive layer is positioned above the metal surface.

13. The method for testing a CMOS transistor according to claim 1, wherein the electrical testing unit includes three electrically-conducting probes that extend from a probe holder through the support plate and the conductive layer to a surface of one of the CMOS transistors.

14. The method for testing a CMOS transistor according to claim 13, further comprising the step of:
moving the electrical testing unit over each of the CMOS transistors formed on the semiconductor wafer.

15. The method for testing a CMOS transistor according to claim 1, wherein the potential difference between the first terminal contact and a third terminal contact is generated by applying voltage between the conductive layer and the third terminal contact, wherein the third terminal contact is the a source contact of the CMOS transistor.

16. The method for testing a CMOS transistor according to claim 1, wherein a ratio between an output voltage at the first terminal contact and the drive potential applied to the conductive layer is measured to test the CMOS transistor.

17. A method for testing a CMOS transistor with an electrical testing unit, the method comprising:
forming the CMOS transistor in a semiconductor substrate of a semiconductor wafer, the CMOS transistor having a first terminal contact and a second terminal contact and a third terminal contact, the second terminal contact being configured as an electrically open control contact, wherein a plurality of CMOS transistors are formed on the semiconductor wafer;
providing the electrical testing unit with a support plate;
forming a conductive layer on the support plate;
positioning a conductive layer above the semiconductor wafer over the control contact;
generating a potential difference between the first terminal contact and a third terminal contact;
capacitively coupling the control contact by applying a drive potential to a conductive layer; and
testing a function of the CMOS transistor by measuring an electrical variable dependent on the capacitive coupling, wherein the support plate is smaller than 6 $cm^2$ in size, and wherein the conductive layer on the support plate comprises less than 70% of the area of the support plate.

* * * * *